United States Patent [19]

Hagen et al.

[11] Patent Number: 5,245,058
[45] Date of Patent: Sep. 14, 1993

[54] PREPARATION OF 1-NITROANTHRAQUINONE-2-CARBOXYLIC ACIDS

[75] Inventors: Helmut Hagen, Frankenthal; Jacques Dupuis, Ludwigshafen; Michael Acker, Heidelberg; Udo Bergmann, Bensheim, all of Fed. Rep. of Germany

[73] Assignee: BASF Aktiengesellschaft, Ludwigshafen, Fed. Rep. of Germany

[21] Appl. No.: 936,211

[22] Filed: Aug. 27, 1992

[30] Foreign Application Priority Data

Aug. 27, 1991 [DE] Fed. Rep. of Germany ....... 4128348

[51] Int. Cl.$^5$ ............................................. C07C 50/24
[52] U.S. Cl. ..................................... 552/250; 562/410
[58] Field of Search ......................... 552/250; 562/410

[56] References Cited

U.S. PATENT DOCUMENTS 3,631,097 12/1971 Christmann, et al. ............. 562/410
4,454,345 6/1984 Jacques ............................... 562/410

Primary Examiner—Marianne M. Cintins
Assistant Examiner—Kimberly J. Kestler
Attorney, Agent, or Firm—Oblon, Spivak, McClelland, Maier & Neustadt

[57] ABSTRACT

1-Nitroanthraquinone-2-carboxylic acids of the general formula I

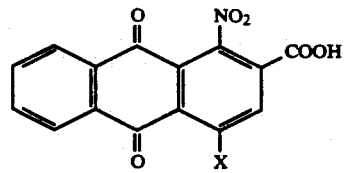

where X is hydrogen, chlorine or bromine, are prepared by oxidizing a 1-nitro-2-methylanthraquinone of the general formula II

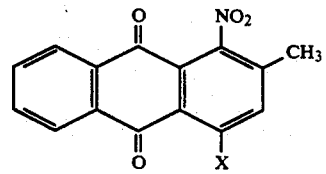

with nitric acid in an organic reaction medium.

6 Claims, No Drawings

PREPARATION OF 1-NITROANTHRAQUINONE-2-CARBOXYLIC ACIDS

The present invention relates to a novel process for preparing 1-nitroanthraquinone-2-carboxylic acids of the general formula I

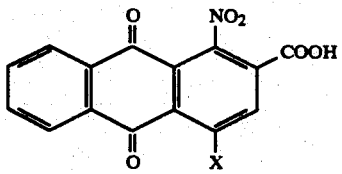

where X is hydrogen, chlorine or bromine, by oxidizing a 1-nitro-2-methylanthraquinone of the general formula II

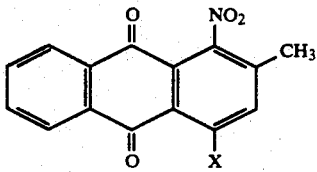

1-Nitroanthraquinone-2-carboxylic acid and 1-nitro-4-haloanthraquinone-2-carboxylic acids are important intermediates for preparing vat dyes such as anthraquinoneazoles, acylaminoanthraquinones and phthaloylacridones.

They are obtainable in various known ways, usually by oxidation of the corresponding 2-methylanthraquinones. As described in DE-A-229 394 and DE-A-2 242 643, the oxidizing agents used are chromium-(VI) salts in inorganic acids. However, these processes have the disadvantage of producing large quantities of chromium(III) salts, necessitating extensive waste water treatment.

It is an object of the present invention to provide 1-nitroanthraquinone-2-carboxylic acids (I) in good yields and good purities in a technically simple and economical manner without heavy metal pollution of the waste water.

We have found that this object is achieved by a process for preparing 1-nitroanthraquinone-2-carboxylic acids of the general formula I

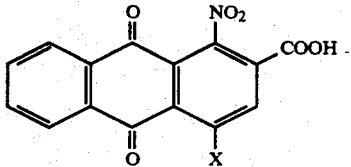

where X is hydrogen, chlorine or bromine, by oxidizing a 1-nitro-2-methylanthraquinone of the general formula II

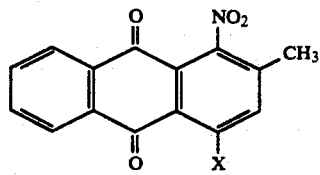

which comprises carrying out the oxidation in an organic reaction medium using nitric acid as oxidizing agent.

The concentration of the nitric acid used in the process of the invention can vary within wide limits, but advantageously its concentration is from 40 to 100% by weight, in particular from 50 to 70% by weight.

Suitable organic reaction media for the process of the invention are in particular benzene derivatives which are liquid at the reaction temperature and do not react with nitric acid. Suitable examples are nitrobenzene, benzoic acid and mixtures thereof. Nitrobenzene is particularly preferred.

The solvent quantity is freely choosable, but it is advisable to employ from 0.5 to 2, preferably from 1 to 1.5, mol of solvent per mole of II.

In general, the reaction is carried out at from 180° to 200° C., preferably at from 185° to 190° C.

The reaction is customarily carried out under atmospheric pressure, but it is also possible to employ superatmospheric pressure.

The process is preferably carried out by heating the 1-nitro-2-methylanthraquinone II in nitrobenzene to 180°-200° C. and adding the nitric acid at that temperature.

The oxidation is advantageously carried on to a conversion of from 50 to 80%, in particular about 70%. The degree of conversion may be monitored in a conventional manner by chromatography. A 70% conversion generally requires from 2 to 6 mol, preferably from 3 to 5 mol, of nitric acid per mole of II.

During the reaction, which in general takes from 8 to 12 hours, dilute nitric acid can be distilled off in a mixture with nitrobenzene.

The process of the invention can be carried out not only batchwise but also continuously.

If nitrobenzene is used as solvent, the reaction mixture can be particularly advantageously worked up for the 1-nitroanthraquinone-2-carboxylic acids by cooling to 100°-120° C., preferably to 105°-110° C. At that temperature the products I are mostly precipitated and can be separated off by filtration, while the unconverted fraction of the starting compounds II remains in solution in the mother liquor and can be reused for a subsequent oxidation.

To remove the nitrobenzene residues from the filter residues of products I, the still moist filter residue is advantageously suspended in water and the nitrobenzene is distilled off with steam. The products I can then be isolated by filtration from the nitrobenzene-free aqueous suspension in a sufficiently pure form for immediate use for further purposes, in particular dye synthesis.

The 1-nitroanthraquinone-2-carboxylic acids are obtained by the process of the invention in good yield and good purity in a technically simple and economical manner.

A particularly preferred use for this process is the preparation of unsubstituted 1-nitroanthraquinone-2-carboxylic acid.

EXAMPLES

Preparation of 1-nitroanthraquinone-2-carboxylic acid

EXAMPLE 1

A mixture of 1069 g (4.1 mol) of 1-nitro-2-methylanthraquinone and 4820 g of nitrobenzene was heated to 190° C. At that temperature 4200 g (3000 ml; 43.3 mol) of 65% by weight nitric acid and 2410 g (2000 ml) of nitrobenzene were metered in separately over 10 h (the amounts used corresponding to a conversion of 70%). At the same time about 3000 ml of 50% by weight nitric acid and about 2000 ml of nitrobenzene were distilled off. On completion of the nitric acid addition the reaction mixture was subsequently stirred for a further 30 min and then cooled down to 110° C.

The 1-nitroanthraquinone-2-carboxylic acid precipitated as a result was filtered off and suspended in 4000 ml of water. After the nitrobenzene still present in the solids had been distilled off with steam, the 1-nitroanthraquinone-2-carboxylic acid was again separated from the aqueous suspension by filtration and dried at 100° C.

This gave 382 g of 1-nitroanthraquinone-2-carboxylic acid with a purity of >98%, which corresponds to a yield of 45%, based on a 70% conversion.

EXAMPLE 2

A mixture of the nitrobenzene mother liquor from the filtration in Example 1 (containing 1.2 mol of unconverted 1-nitro-2-methylanthraquinone and unprecipitated product) and 748 g (2.8 mol) of fresh 1-nitro-2-methylanthraquinone was reacted with nitric acid as described in Example 1.

The subsequent workup was likewise carried out as described in Example 1.

This gave 594 g of 1-nitroanthraquinone-2-carboxylic acid with a purity of >98%, which corresponds to a yield of 70%, based on a 70% conversion.

We claim:

1. A process for preparing 1-nitroanthraquinone-2-carboxylic acids of the general formula I

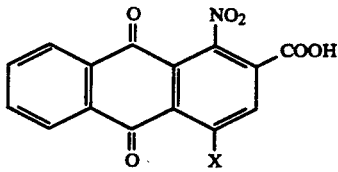

where X is hydrogen, chlorine or bromine, by oxidizing a 1-nitro-2-methylanthraquinone of the general formula II

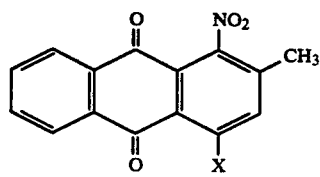

which comprises carrying out the oxidation in an organic reaction medium using nitric acid as oxidizing agent.

2. A process as claimed in claim 1, wherein the reaction medium used comprises nitrobenzene, benzoic acid or a mixture thereof.

3. A process as claimed in claim 1, wherein the oxidizing agent used comprises 40–100% strength by weight nitric acid.

4. A process as claimed in claim 1, wherein the oxidation is carried out at from 180° to 200° C.

5. A process as claimed in claim 1, wherein the oxidation is carried on to a conversion of from 50 to 80%.

6. A process as claimed in claim 1 employed for preparing 1-nitroanthraquinone-2-carboxylic acid.

* * * * *